(12) United States Patent
Miller et al.

(10) Patent No.: US 8,232,103 B2
(45) Date of Patent: Jul. 31, 2012

(54) MERGE STOP GATE FOR AN AUTOMATED LABORATORY SAMPLE HANDLING WORKSYSTEM

(75) Inventors: Kerry Lynn Miller, Elkton, MD (US); Frank Jay Robb, Middletown, DE (US); Peter Louis Gebrian, Wilmington, DE (US); Sandor Lajos Kovacs, Middletown, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 1422 days.

(21) Appl. No.: 11/500,672

(22) Filed: Aug. 8, 2006

(65) Prior Publication Data

US 2008/0038827 A1 Feb. 14, 2008

(51) Int. Cl.
*G01N 35/04* (2006.01)
(52) U.S. Cl. .............. 436/47; 436/43; 422/63; 422/65; 198/465.1; 198/867.11; 198/867.13; 198/369.5
(58) Field of Classification Search .................. None
See application file for complete search history.

(56) References Cited

U.S. PATENT DOCUMENTS

| | | | |
|---|---|---|---|
| 2,936,062 A | 5/1960 | M.J. Wilcox | |
| 4,805,469 A | 2/1989 | Commarmot | |
| 5,087,423 A | 2/1992 | Ishibashi | |
| 5,178,834 A | 1/1993 | Kagayama et al. | |
| 5,209,903 A | 5/1993 | Kanamori et al. | |
| 5,445,037 A * | 8/1995 | Itoh .......................... | 73/864.25 |
| 5,623,415 A | 4/1997 | O'Bryan et al. | |
| 5,846,491 A | 12/1998 | Choperena et al. | |
| 5,876,670 A | 3/1999 | Mitsumaki et al. | |
| 5,941,366 A * | 8/1999 | Quinlan et al. ............ | 198/465.1 |
| 6,019,945 A | 2/2000 | Ohishi et al. | |
| 6,060,022 A | 5/2000 | Pang et al. | |
| 6,117,683 A | 9/2000 | Kodama et al. | |
| 6,290,907 B1 | 9/2001 | Takahashi et al. | |
| 6,599,749 B1 | 7/2003 | Kodama et al. | |
| 2004/0124109 A1 * | 7/2004 | Hassinen et al. ........... | 206/443 |
| 2005/0207937 A1 * | 9/2005 | Itoh ............................ | 422/63 |
| 2006/0142090 A1 | 6/2006 | Henry | |

FOREIGN PATENT DOCUMENTS

| | | |
|---|---|---|
| JP | H02-138015 A | 5/1990 |
| JP | H05-014021 A | 2/1993 |
| JP | 3059194 B | 3/1999 |
| JP | 2006-103867 A | 4/2006 |

OTHER PUBLICATIONS

English Abstract of JP H02-138015A.
English Abstract of JP 2006-103867A.

* cited by examiner

*Primary Examiner* — P. Kathryn Wright
(74) *Attorney, Agent, or Firm* — Leland K. Jordan (57) ABSTRACT

A method for replacing a first sample carried on a moving secondary conveyor onto a moving primary conveyor at a potential interference point while the primary conveyor is transporting a second sample.

2 Claims, 12 Drawing Sheets

MERGE STOP GATE FOR AN AUTOMATED LABORATORY SAMPLE HANDLING WORKSYSTEM

FIELD OF THE INVENTION

The present invention relates to an automated clinical sample handling worksystem with two or more independent processing stations having samples supplied thereto by an automated conveyor system. More particularly, the present invention relates to a method for enabling samples to return to the conveyor from a processing station without interfering with samples on the conveyor.

BACKGROUND OF THE INVENTION

Clinical diagnostic analyzers are being developed with increasing levels of complexity and sophistication in order to fully automated the performance of chemical assays and immunoassays of biological fluid samples such as urine, blood serum, plasma, cerebrospinal liquids and the like, these fluid samples almost universally being contained in open or capped sample tubes. Generally, chemical reactions between an analyte in a patient's biological sample and reagents used during performing the assay result in generating various signals that can be measured by the analyzer. From these signals the concentration of the analyte in the sample may be calculated.

A wide variety of automated chemical analyzers are known in the art and are continually being improved to increase analytical menu and throughput, reduce turnaround time, and decrease requisite sample volumes. See for example, U.S. Pat. Nos. 6,103,193, and 6,027,691 and 5,482,861. Such improvements, while necessary in themselves, may be hampered if sufficient corresponding advances are not made in the automation of pre-analytical sample preparation and handling operations like sorting, batch preparation, centrifugation of sample tubes to separate sample constituents, cap removal to facilitate fluid access, and the like.

Automated sample pre-treatment systems generally include the use of conveyor systems for conveying specimens to analyzers, such as those described in U.S. Pat. Nos. 5,178,834, and 5,209,903. Typical of such systems, a sample is transported to an analyzer by a primary conveyor and either removed from the primary conveyor by a robotic-like device and placed into a sampling area of an adjacent analyzer or may be shuttled onto an analyzer-specific conveyor that transports the sample to the sampling area of an adjacent analyzer. In the later instance, when sufficient sample aliquots have been removed from the sample, the sample is returned to the primary conveyor and transferred thereto from the analyzer-specific conveyor.

As automated clinical chemistry sample handling workstations become increasingly complex, the number of instances wherein samples interfere with one another during transportation processes also increase. Clearly, a problem to be avoided is any form of interference between the sample transferring from the analyzer-specific conveyor with samples already on the primary conveyor and being transported thereby.

U.S. Pat. No. 6,019,945 discloses a transfer mechanism for transferring a sample container holder between a conveyor line and a sampling area formed in each of several analyzers, the transfer mechanism being connectable to each one of the plurality of analyzers. At least two analyzers units are different from one other in either the types of reagent supply means, the number of analysis items that can be analyzed, the number of tests that can be processed in a unit time, or the species of samples to be processed.

U.S. Pat. No. 5,087,423 discloses a plurality of analyzing modules, a plurality of analyzing routes and at least one bypass route bypassing at least one analyzing module are arranged. Each analyzing module is capable of analyzing samples with respect to one or more items, and samples successively supplied from the introduction sides of the modules are selectively delivered into each module.

U.S. Pat. No. 6,060,022, automatically presents pre-treated samples in open containers to robotic devices operated in conjunction with independent stand-alone analyzers. In order to provide precise and accurate handling of the sample tubes, it is critical to position and align the tubes within a sample tube carrier accurately so that the various robotic handling devices may automatically and consistently remove or replace tubes from tube carriers as needed.

Although these prior art systems have advanced sample handling and processing throughput, what has not been addressed is the challenge of replacing a sample onto a moving conveyor belt while the belt is conveying other samples without adversely affecting either of the two samples.

SUMMARY OF THE INVENTION

The present invention provides a method for replacing a sample onto a moving primary conveyor while the conveyor is conveying other samples without adversely affecting either of the two samples. As a first step, any samples transported on the primary conveyor are stopped or slowed down at a position upstream of the sample transferring from an analyzer-specific conveyor onto a primary conveyor. As a second step, samples on the primary conveyor are stopped or slowed down in a manner that eliminates abrupt or uncontrolled motions that might otherwise disturb the sample. This new method for operating a sample handling worksystem provides an improved capability to operate a clinical laboratory's automated sample handling worksystem by improving the overall reliability and efficiency of moving and processing samples.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
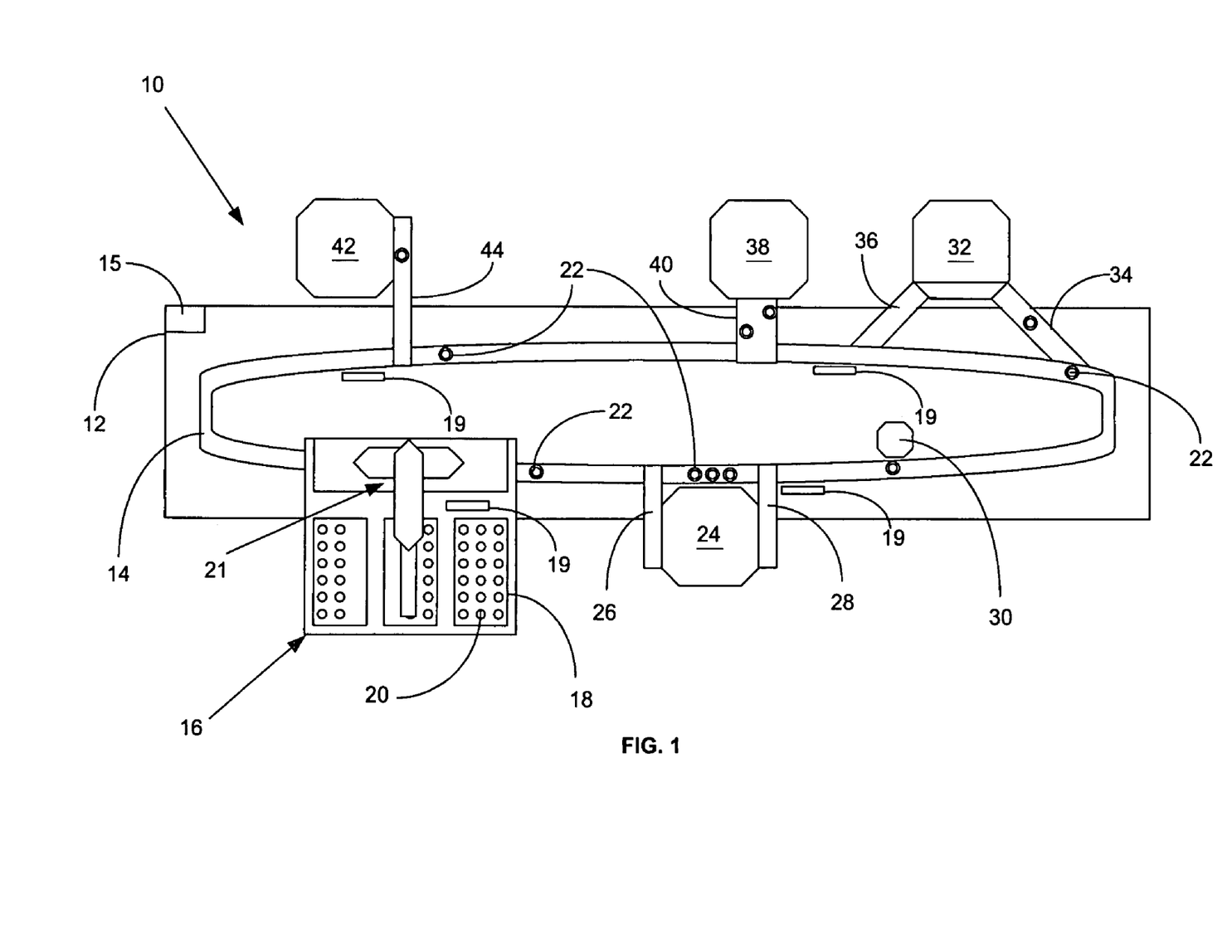
FIG. 1 is a simplified schematic plan view of an automated sample handling system including a conveyor controlled in cooperation with several chemical analysis pre-treatment devices and analyzers in which the present invention may be employed advantageously.

Referring to FIG. 1, there is illustrated an automated clinical chemistry sample handling worksystem 10 capable of automatically pre-processing as necessary multiple sample containers 20, typically sample test tubes, contained in multiple sample racks 18 so as to practice the present invention. Typically, patient specimens to be automatically processed are provided to sample handling system 10 in multiple containers, such as test tubes, which can be capped. Each of the sample containers 20 is provided with container identification indicia, such as a bar code, indicating a patient's identification, as well as, optionally, the assay procedures to be accomplished upon the sample therein. The containers are generally held in one or more holders such as racks that may have additional identification indicia thereon.

The sample handling worksystem 10 comprises an operating base 12 on which a belt-like conveyor track 14 transports a plurality of individual sample tube containers 20 carried in sample tube carriers 22 from a sample tube loading/unloading station 16 to an automated centrifuge 24 to an automated tube de-capper 30 for automatically removing caps from capped sample containers 20 and to one or more conventional clinical analyzers 32, 38, and 42 before returning each sample container 20 to the sample tube loading/unloading robotic station 16. It will be understood that more than three analyzers 32, 38, and 42 may be linked by conveyor track 14, but for purposes of simplicity, only three are shown. The sample handling worksystem 10 has a number of sensors, not illustrated, for detecting the location of a sample tube container 20 by means of identifying indicia placed on or within each sample tube carrier 22. Conventional bar-code readers may be employed in such tracking operations.

Centrifuge 24 and each analyzer 38, 42 and 32 are generally equipped with various robotic mechanisms 26 and 28, 40 and 44 or analyzer tracks 34 and 36, respectively, for removing a sample tube carrier 22 from conveyor track 14, moving the sample tube carrier 22 to and from centrifuge 24, to and from or into and out from analyzers 38, 42 and 32, respectively. Typically, the loading/unloading station 16 includes at least two robotic arms 21 conventionally equipped with clamping robotic hands.

The sample handling worksystem 10 is controlled by a conventional computer 15 preferably a microprocessor based central processing unit CPU 15 housed as part of or separate from the system 10 to move the sample tube carrier 22 to each operating station 24, 30, 32, 38, 42 and 16 whereat various types of assay processing occurs. CPU 15 controls sample handling system 10 according to software, firmware, or hardware commands or circuits like those used on the Dimension® clinical chemistry analyzer sold by Dade Behring Inc. of Deerfield, Ill., and are typical of those skilled in the art of computer-based electromechanical control programming.

Figure 2:
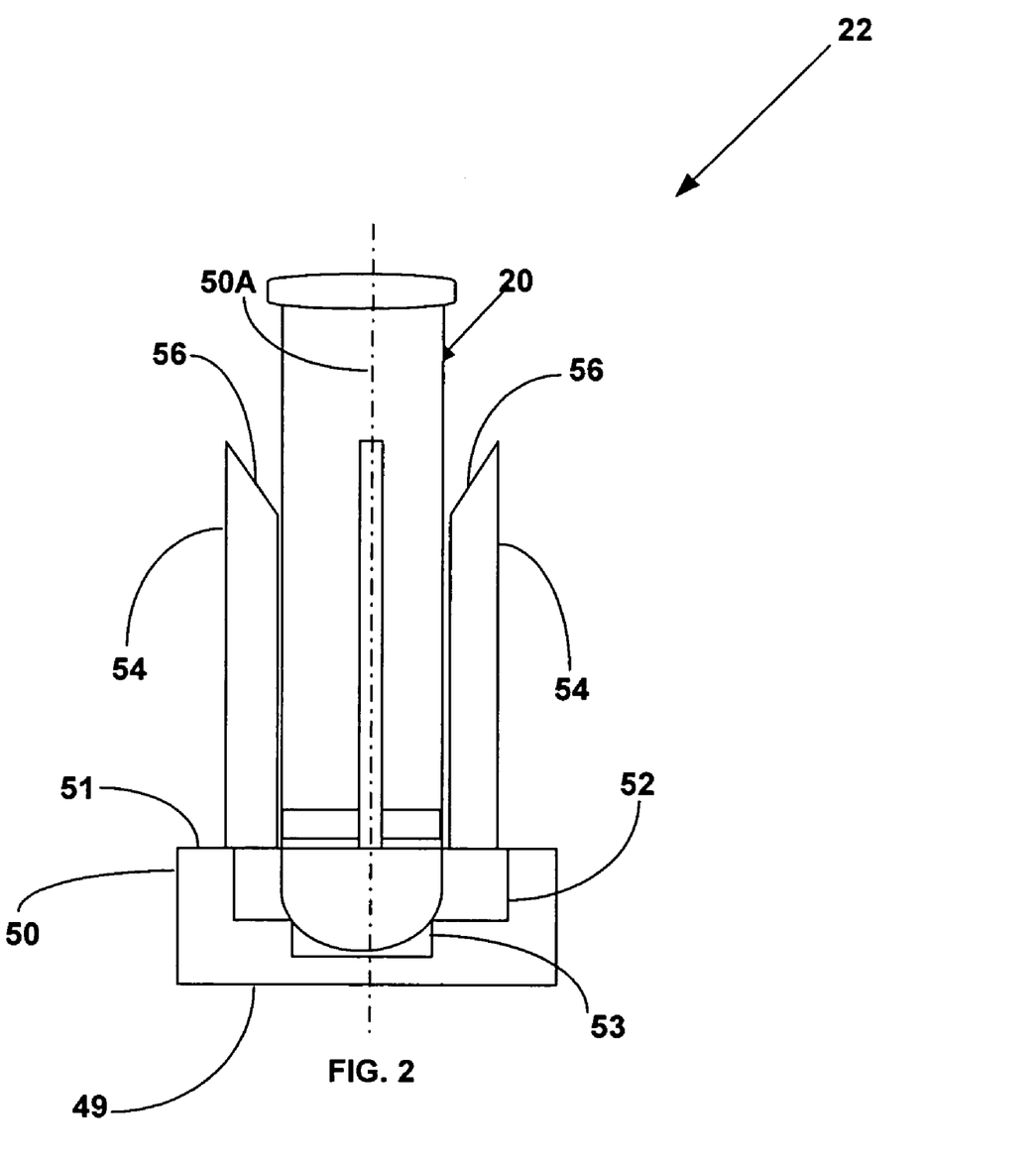
FIG. 2 is a simplified elevation view of a sample tube carrier adapted for use in the sample handling system of FIG. 1.

FIG. 2 is an elevation view of an exemplary sample tube carrier 22 for transporting a cylindrical sample tube container 20 shown in phantom lines having a tube diameter and a tube longitudinal height, the carrier comprising a generally cylindrical lower carrier body 50 having a central axis 50A and a cylindrical hole 52 formed along said axis depending from a top surface 51 of the carrier body 50 towards a bottom surface 49 of the carrier body 50. An optional recess 53 centered along axis 50A may be seen, recess 53 provided to accommodate the rounded bottom typically found on clinical sample tube containers 20. Carrier body 50 has at least two vertically oriented arms 54 symmetrically disposed within the cylindrical hole 52 and extending a distance upwards above the top surface 51. The vertically oriented arms 54 include a tapered upper end 56 seen tapered downwardly towards the central axis 50A.

Figure 3:
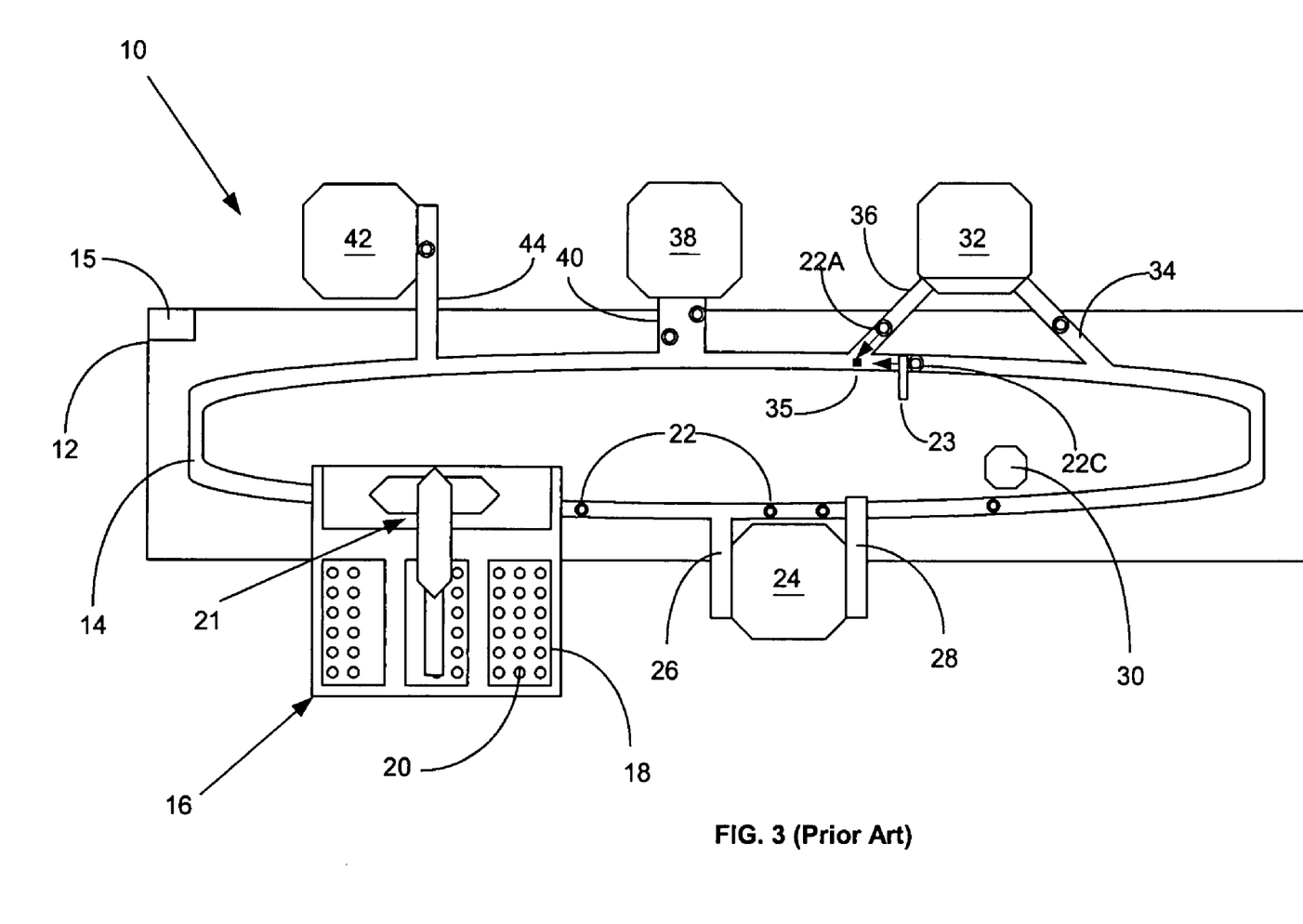
FIG. 3 is a simplified plan view of a prior art approach to handle samples within the sample handling system of FIG. 1.
Figure 4:
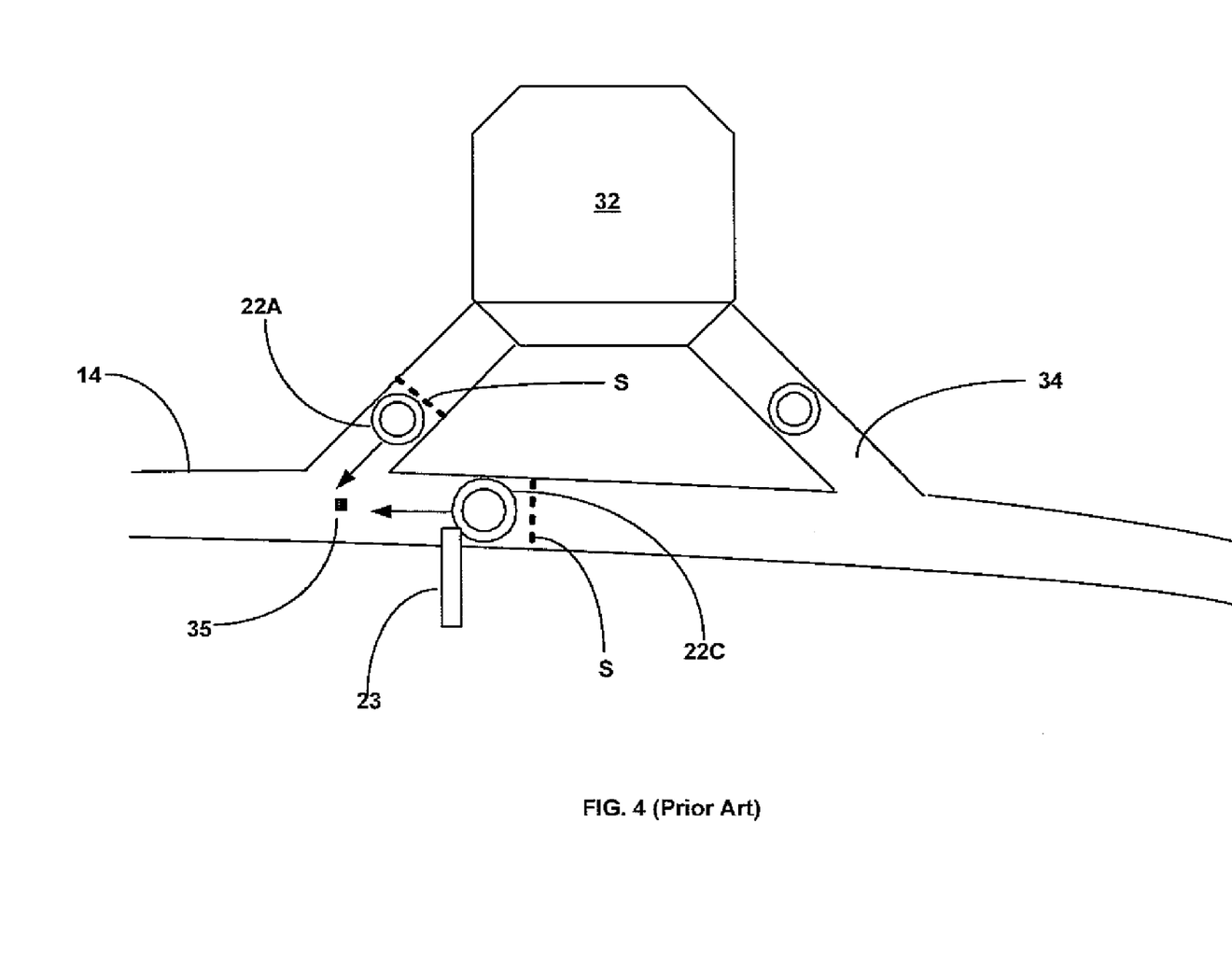
FIG. 4 is an enlarged view of a portion of FIG. 3 illustrating a first failure mode of the prior art.
Figure 5:
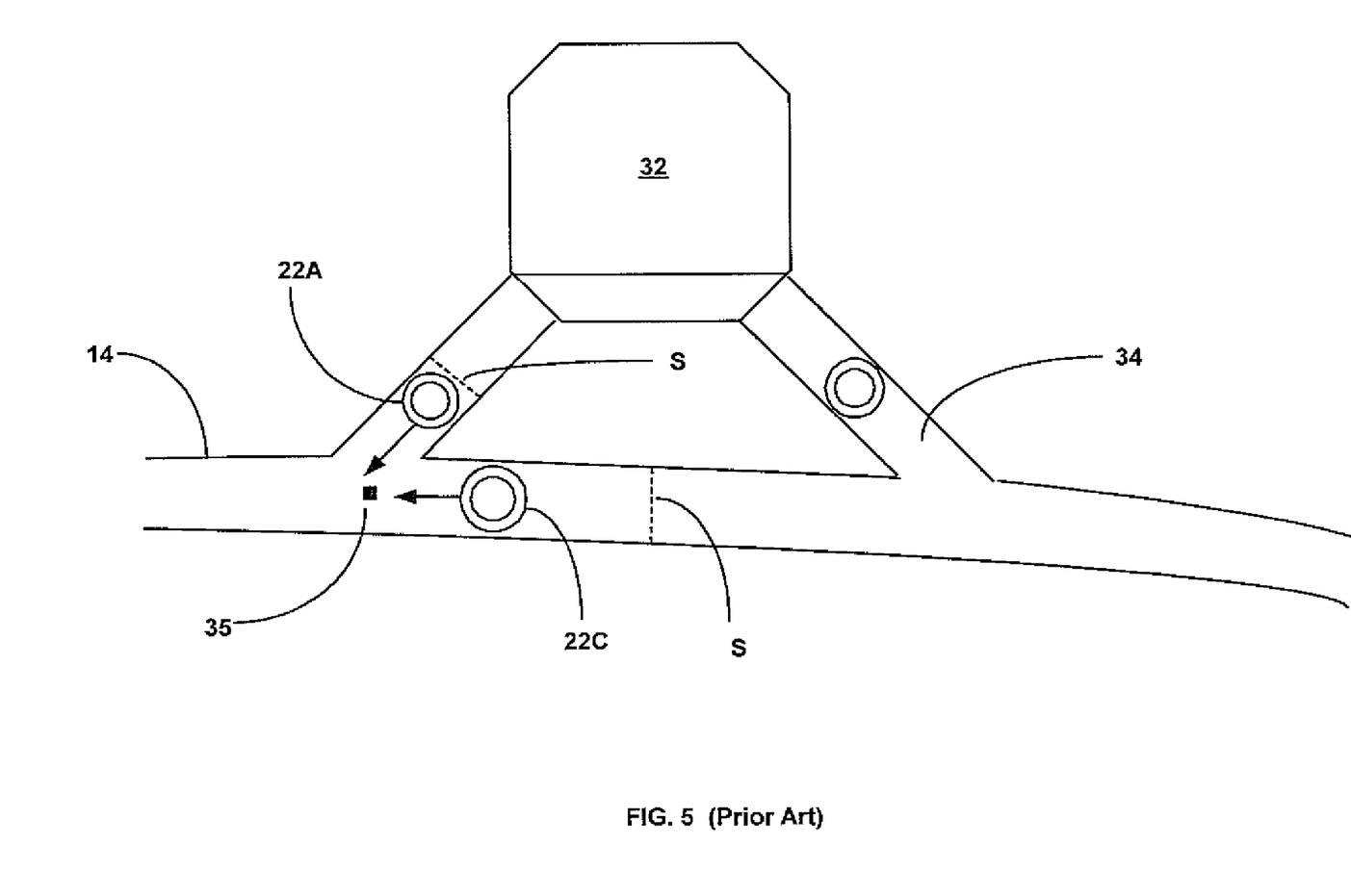
FIG. 5 is an enlarged view of a portion of FIG. 3 illustrating a second failure mode of the prior art.

FIG. 3 illustrates a typical instance addressed by the present invention in which a sample tube carrier 22A, having been analyzed as requested by clinical analyzer 32, is being returned along analyzer track 36 to conveyor track 14 (illustrated herein as moving in a counter-clockwise direction) before being additionally tested and/or removed from conveyor track 14 and/or retained in storage within system 10. Conventional sensors S, typically light beam or proximity type, are positioned strategically along conveyor track 14 in a manner to anticipate a potential interference at interference point 35 between sample tube carrier 22A entering conveyor track 14 and sample tube carrier 22C being transported along conveyor track 14. In prior art systems, illustrated in FIG. 3, it is common practice to install a sensor-actuated plunger 23 adjacent conveyor track 14 and adapted to extend above the surface of conveyor track 14 stopping movement of sample tube carrier 22C prior to reaching interference point 35. Alternately sensor-actuated plunger 23 may be installed adjacent analyzer track 36 and adapted to extend above the surface of analyzer track 36 stopping movement of sample tube carrier 22A prior to reaching interference point 35. As seen in enlarged FIG. 4, a problem encountered in such prior art solutions is that the plunger 23 may be "late" and physically contact sample tube carrier 22C in a glancing manner that causes the sample tube 20 to be tilted and possibly spill liquid patient sample contained therein. Alternately, as seen in FIG. 5, plunger 23 may be "even later" and physically contact sample tube carrier 22C in a pinning manner that causes sample tube carrier 22C to be pinned against a wall or rail normally positioned alongside conveyor track 14.

These and similar problems are eliminated by the present invention in which each and every sample tube carrier 22C that is transported along conveyor track 14 is led through a generally propeller-shaped turnstile 60 (FIG. 10) as it approaches a potential interference point 35. The generally propeller-shaped turnstile 60 acts to cradle sample tube carriers 22C and is adapted with a suitable plunger so that its rotation may be stopped at any time a sample tube carrier 22A approaches potential interference point 35. What has been discovered is that if a fast lateral force is applied to the sample, the potential for re-suspension and/or spill (along with the potential for cross contamination of samples) is increased. Prior art stop gates that have motion generally perpendicular to the sample path potentially causes such problems. The present invention avoids such problems by providing a gate that has that a gate orientation designed to slow down the gate speed or to provide some degree of elasticity to the plunger so that there is not enough force to cause spills or re-suspension. This is achieved in the present invention by having the stop cylinder stop or slow down the turnstile thereby stopping or slowing down the sample. By using the turnstile of the present invention, the sample may be slowed down by reducing the drag of the braking force.

Figure 6:
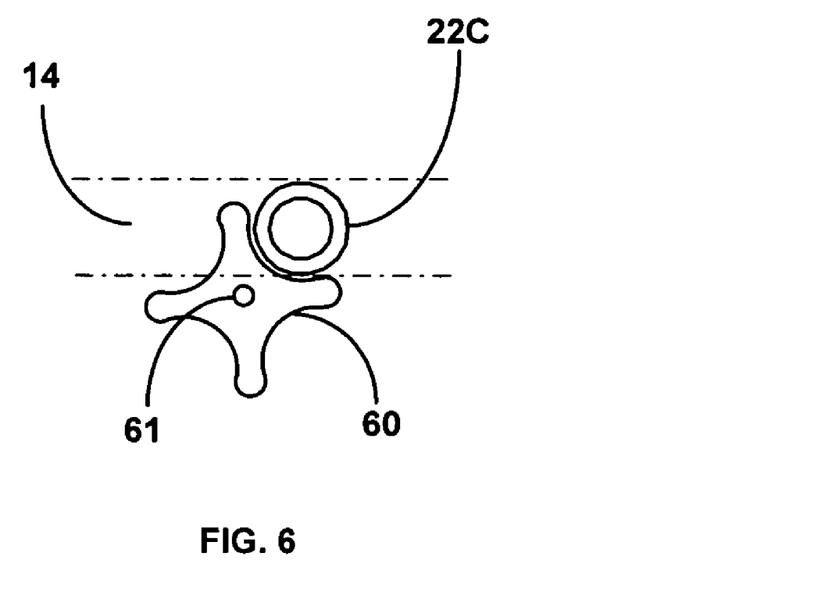
FIGS. 6-6A-6B-6C is a schematic view of the present invention for handling sample within the automated sample handling system of FIG. 1.
Figure 6A:
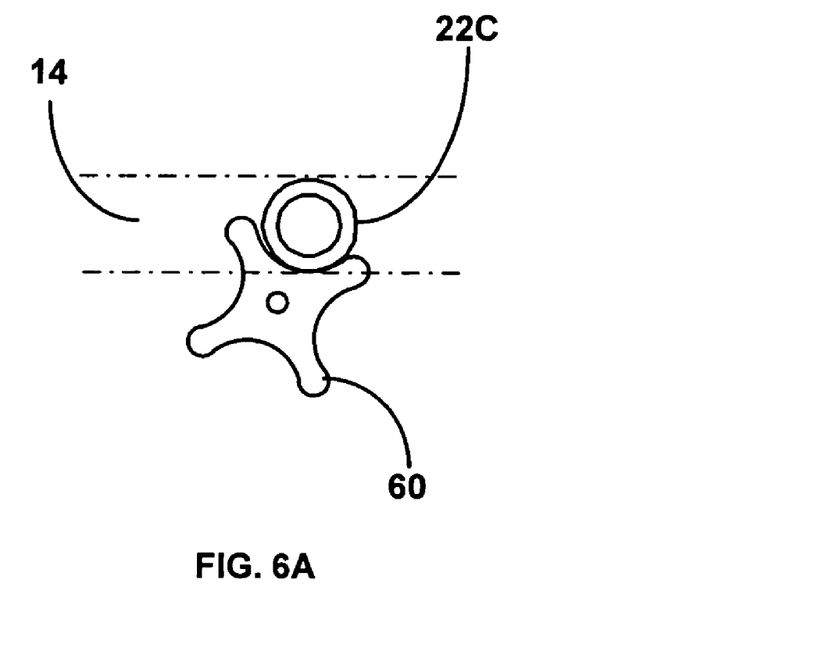
Figure 6B:
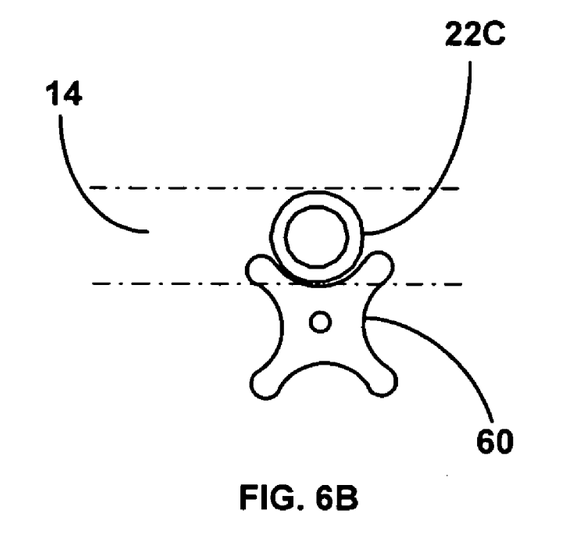
Figure 6C:
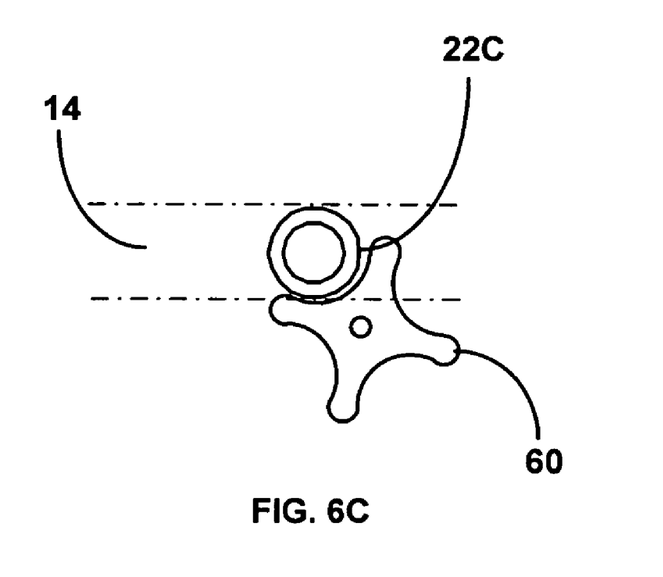

FIG. 6 schematically illustrates generally propeller-shaped rotatably mounted adjacent conveyor track 14 around a mounting pin 61 that is exemplary of the present invention. FIGS. 6A-6B-6C schematically illustrate how generally propeller-shaped 60 rotates "clockwise" as sample tube carrier 22C traverses along conveyor track 14.

Figure 7:
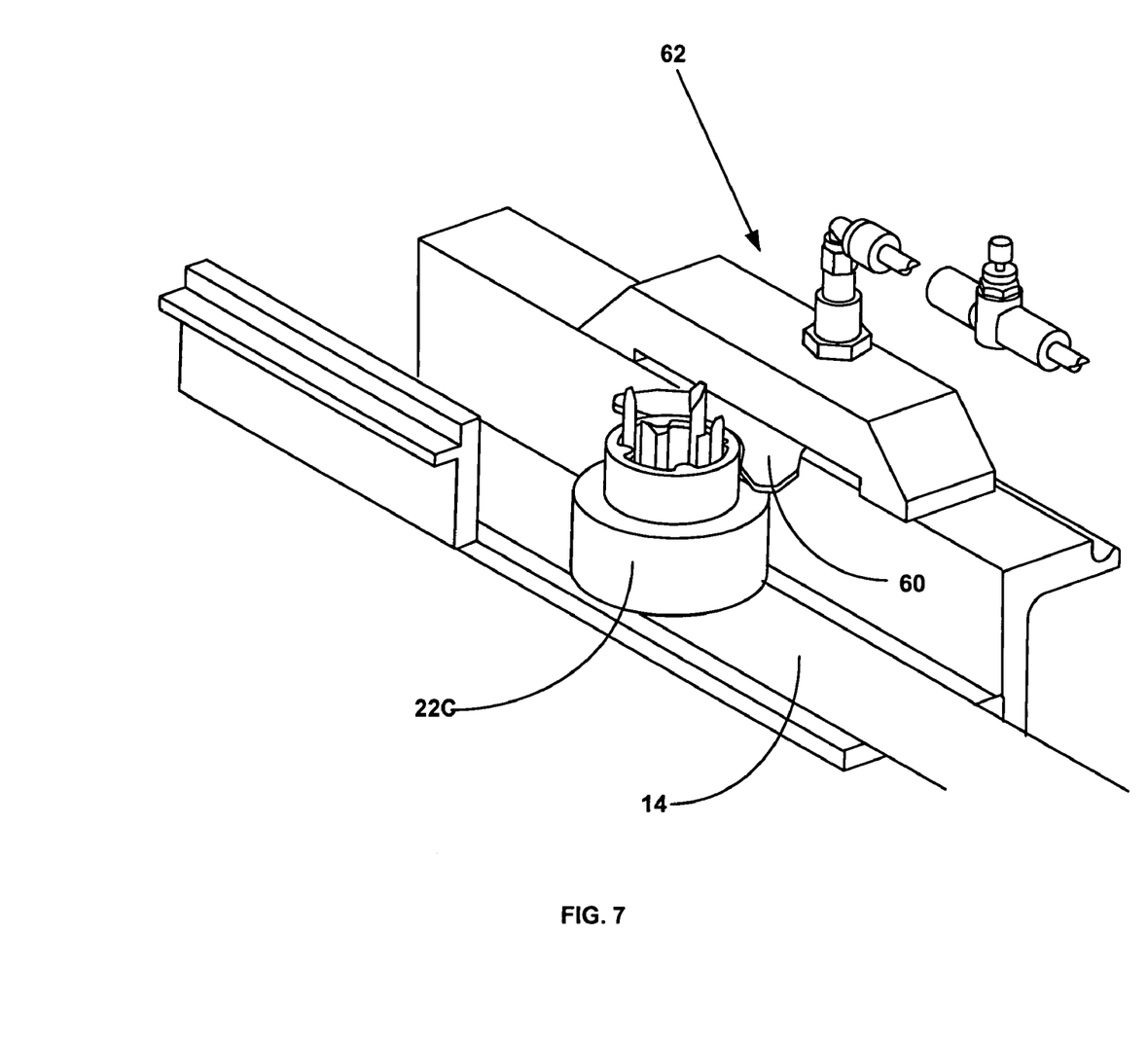
FIG. 7 is a cut-away perspective view of the sample handling device of FIG. 6.
Figure 8:
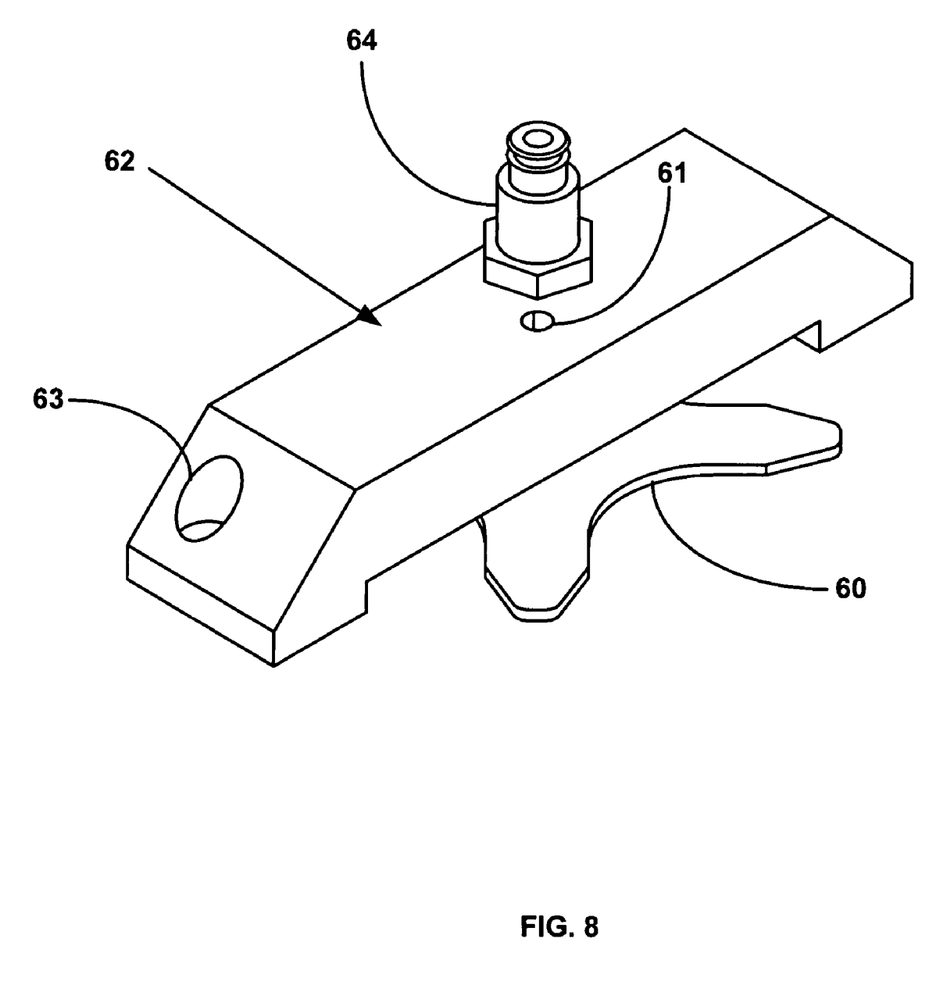
FIG. 8 is an enlarged perspective view of the sample handling device of FIG. 6.

FIG. 7 is a cut-away perspective illustration showing sample tube carrier 22C cradled within turnstile 60 in an orientation comparable to the schematic illustration in FIG. 6B. A turnstile locking mechanism 62 (FIG. 9) is provided in order to arrest rotation of turnstile 60 so that movement of sample tube carrier 22C may be stopped at any time a sample tube carrier 22A approaches potential interference point 35. Alternately, an adjustable drag force may be applied to turnstile 60 so that sample tube carrier 22C may be slowed down. Drag forces may be applied using the plunger 65 (FIG. 9) adjusted to slow the turnstile 60 (FIG. 9) with pin 66 (FIG. 9) rather than stop it completely. FIG. 8 is a simplified view of FIG. 7 illustrating turnstile 60 in position beneath locking mechanism 62, the locking mechanism 62 comprising a mounting bracket 64 for supporting an actuatable plunger 65 positioned so that pin 66 of plunger 65 may be thrust through opening 67 in bracket 64 and locking rotation of turnstile 60.

Figure 10:
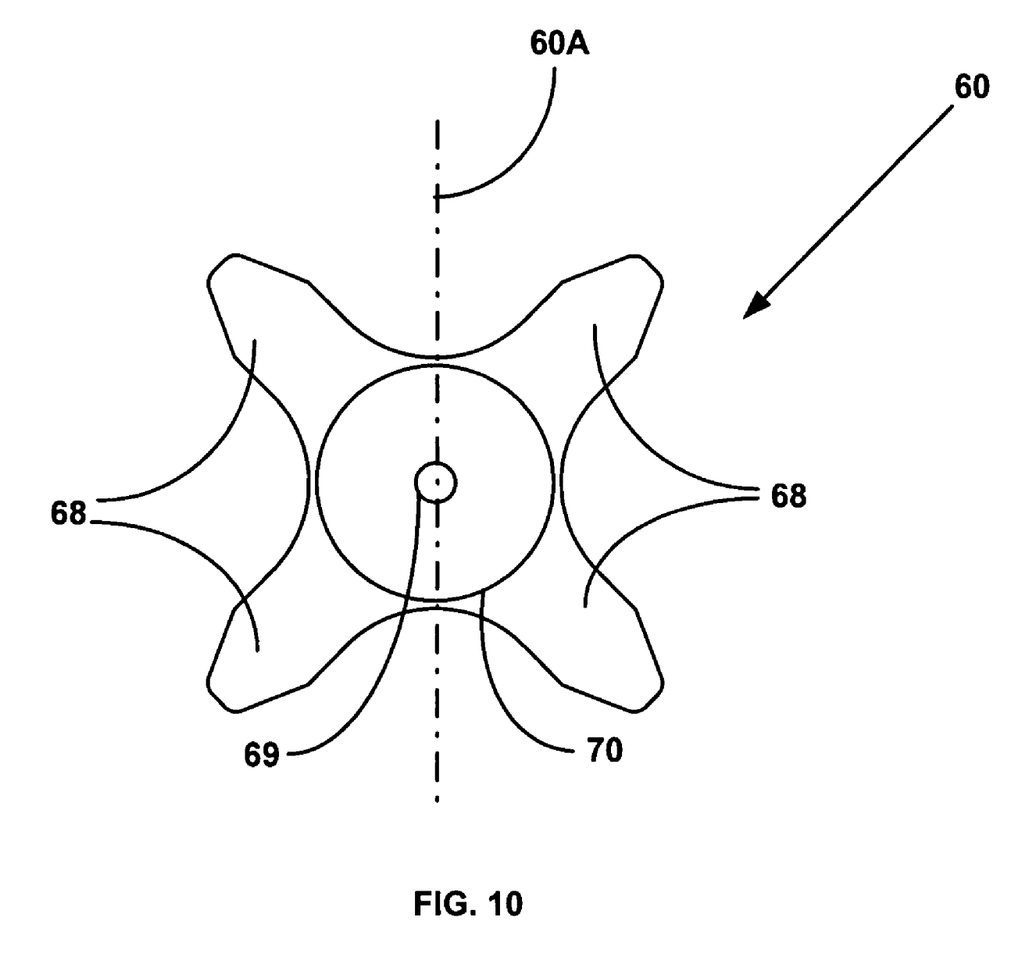
FIG. 10 is top plan view of a key feature of the sample handling device of FIG. 6; and, FIG. 11 illustrates the sample handling device of FIG. 6 installed on the sample handling system of FIG. 1.

FIG. 10 is an exemplary illustration of turnstile 60 comprising two pairs of radially extending blades 68 symmetrically disposed about a central axis 60A. A mounting pin hole 69 sized to accept pin 61 is centered in a circular mounting pad 70 also symmetrically disposed about central axis 60A.

Figure 9:
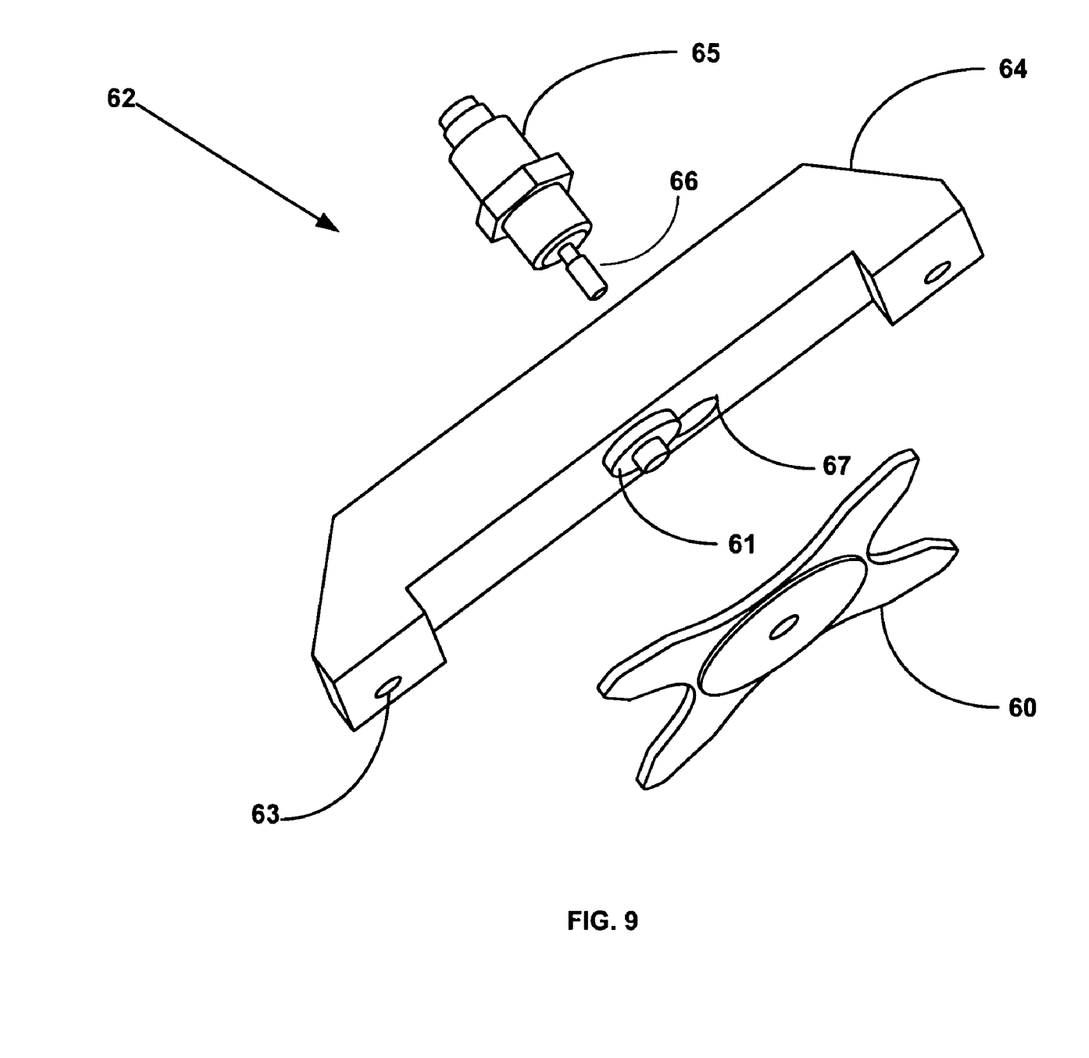
FIG. 9 is an exploded perspective view of the sample handling device of FIG. 6.
Figure 11:
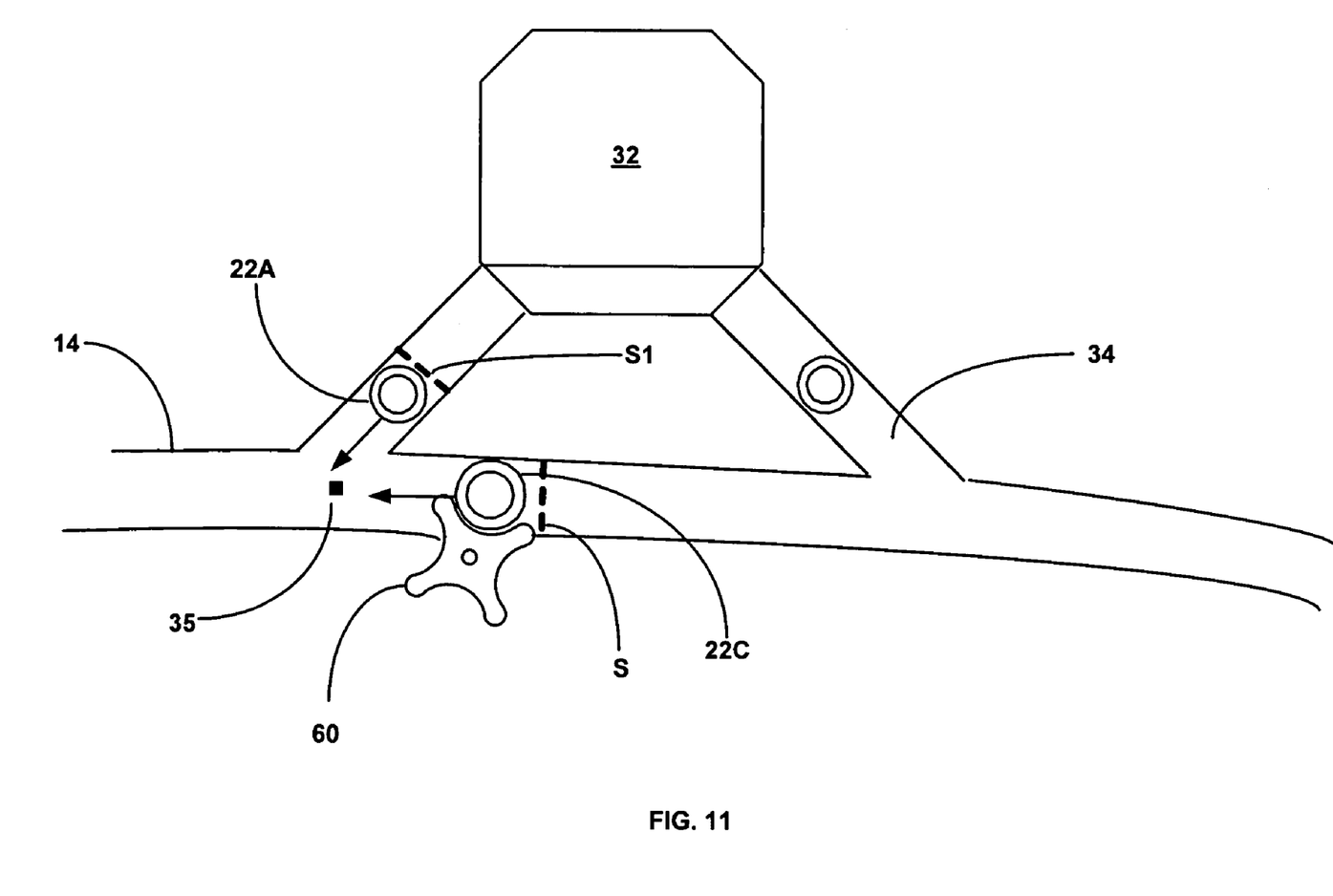

In operation, described in conjunction with FIGS. 9 and 11, actuatable plunger 65 of turnstile locking mechanism 62 is normally un-activated so that turnstile 60 may freely rotate on pin 61 allowing sample tube carriers 22C to be transported along conveyor track 14 through interference point 35 without being stopped. Alternately, a braking force may be applied to turnstile 60 so that it slowly rotates on pin 61 causing sample tube carriers 22C to be slowed down as they are transported along conveyor track 14 through interference point 35. In the event sensor S1 detects another sample tube carrier 22A released from analyzer 32 and approaching interference point 35, plunger 65 of turnstile locking mechanism 62 is activated so that pin 66 is thrust through opening 67, thereby and locking rotation of turnstile 60 and preventing sample tube carriers 22C from being transported along conveyor track 14 through interference point 35. Plunger 65 may be activated by conventional means such as by air pressure or electromagnetic solenoid. After sample tube carrier 22A has passed through interference point 35, plunger 65 is un-activated so that turnstile 60 may again freely rotate and sample tube carriers 22C may be freely transported along conveyor track 14.

Those skilled in the art will appreciate that the embodiments of the invention disclosed herein are illustrative of the principles of the invention and that other modifications may be employed which are still within the scope of the invention. For example, obvious variants of the invention would include turnstile 60 comprising three radially extending blades 68 as might be preferable in the instance of larger diameter sample tube carriers 20. Another obvious variant of the invention would include any propeller-shaped turnstile comprising multiple blades rotatably mounted proximate the primary conveyor.

What is claimed is:

1. A method for replacing a first sample carried on a moving secondary conveyor onto a moving primary conveyor at a potential interference point while the primary conveyor is transporting a second sample by:

stopping the second sample transported on the primary conveyor at position upstream of the potential interference point until the first sample has passed the potential interference point, wherein stopping the second sample comprises:

installing a rotatable turnstile comprising two pairs of radially extending blades symmetrically disposed about the central axis of a circular plate so that a pair of radially extending blades cradles the samples at a location alongside the primary conveyor and upstream of the potential interference point;

causing the second sample carried on the primary conveyor to engage the rotatable turnstile; and, arresting the rotatable turnstile at any time the first sample moving on the secondary conveyor approaches the potential interference point.

2. A method for replacing a first sample carried on a moving secondary conveyor onto a moving primary conveyor at a potential interference point while the primary conveyor is transporting a second sample by:

slowing down the second sample transported on the primary conveyor at position upstream of the potential interference point until the first sample has passed the potential interference point, slowing down the second sample comprises:

installing a rotatable turnstile comprising two pairs of radially extending blades symmetrically disposed about the central axis of a circular plate so that a pair of radially extending blades adapted to cradle the samples at a location alongside the primary conveyor and upstream of the potential interference point;

causing the second sample carried on the primary conveyor to engage the rotatable turnstile; and, partially arresting the rotatable turnstile at any time the first sample moving on the secondary conveyor approaches the potential interference point.

* * * * *